United States Patent [19]

Dennis

[11] Patent Number: 5,605,807
[45] Date of Patent: Feb. 25, 1997

[54] PROCESS FOR SCREENING FOR MALIGNANT TUMORS BY DETERMINING THE AMOUNT OF GLCNAC TRANSFERASE V ACTIVITY

[75] Inventor: James W. Dennis, Etobicoke, Canada

[73] Assignee: Mount Sinai Hospital Corporation, Toronto, Canada

[21] Appl. No.: 304,952

[22] Filed: Sep. 13, 1994

Related U.S. Application Data

[60] Division of Ser. No. 571,069, Aug. 23, 1990, Pat. No. 5,427,914, which is a continuation-in-part of Ser. No. 188,574, Apr. 28, 1988, abandoned.

[51] Int. Cl.$^6$ .............................. C12Q 1/48; G01N 33/48
[52] U.S. Cl. .............................. 435/15; 435/810; 436/64; 436/813
[58] Field of Search ................................. 435/7.9, 15, 35, 435/200, 810; 436/64, 808, 813, 827; 536/4.1

[56] References Cited

U.S. PATENT DOCUMENTS

| | | | |
|---|---|---|---|
| 4,971,905 | 11/1990 | Holmes | 435/15 |
| 5,173,407 | 12/1992 | Uemura | 435/15 |
| 5,206,356 | 4/1993 | Pierce | 536/53 |

OTHER PUBLICATIONS

Dennis J., Oncogenes Conferring Metastatic Potential . . . Oncogene (1989) 4 853–860.

*Primary Examiner*—Ralph J. Gitomer

[57] ABSTRACT

A process is provided for screening for a malignant tumor. The process comprises the steps of determining the amount of GlcNAc transferase V activity in a tumor sample by reacting the GlcNAc transferase V in a tumor sample with an acceptor substrate and a sugar nucleotide donor to produce a detectable change, and detecting the change. The acceptor substrate is an oligosaccharide, a glycopeptide or a glycoprotein having the structure GlcNAc β1-2Man α1-6Man-$R_1$. $R_1$ is GlcNAc β1-4GlcNAc with or without fucose or a synthetic linker. The sugar nucleotide donor is uridine diphospho-N-acetylglycosamine. The amount of GlcNAc transferase V activity in the sample is thereby determined. A determination of the malignancy of the tumor is made by comparing the amount of GlcNAc transferase V activity in the sample with an amount of GlcNAc transferase V associated with normal tissues or with known malignant tumors. A diagnostic kit for screening for a malignant tumor is provided. The kit comprises an acceptor substrate and a sugar nucleotide donor to interact with GlcNAc transferase V in a tumor sample to produce a detectable change, and means for detecting the change.

10 Claims, 14 Drawing Sheets

(9 of 14 Drawings in Color)

PROCESS FOR SCREENING FOR MALIGNANT TUMORS BY DETERMINING THE AMOUNT OF GLCNAC TRANSFERASE V ACTIVITY

This is a divisional of U.S. application Ser. No. 07/571,069 filed Aug. 23, 1990 now U.S. Pat. No. 5,427,914 which in turn, is a continuation-in-part of U.S. Pat. application Ser. No. 07/188,574 filed Apr. 29, 1988 now abandoned.

BACKGROUND OF THE INVENTION

This invention relates to a process for the determination of the malignant potential of a tumor, and diagnostic kits for carrying out the process. The process is suitable for the sensitive and specific determination of the malignant potential of a tumor.

Neoplastic transformation has been associated with increased synthesis and expression of larger (Asn)-linked oligosaccharides. (L. Warren et al., Biochem. Biophys. Acta. 516, p. 97, 1978; U. V. Santer and M. C. Glick, Biochemistry 18, p. 2533, 1979; J. G. Collard et al., Int. J. Cancer 35., p. 207, 1985; L. Warren et al. Proc. Natl. Acad. Sci. U.S.A. 69., p. 1838, 1972; W. K. Van Beek et al., Nature (London) 253, p. 457, 1975). Such changes have been detected in both rodent (L. Warren et al., supra; U. V. Santer and M. C. Glick, supra; and, J. G. Collard et al., supra) and human tumor cells (W. K. Van Beek et al., supra) transformed by chemical mutagens (L. Warren et al., supra), mutagenic viruses (U. V. Santer and M. C. Glick, supra), or by transfection with DNA obtained from neoplastic cells (J. G. Collard et al., supra). The change in size in a number of studies has been attributed to an increase in sialic (neuraminic) acid content of the structures (L. Warren et al., Proc. Natl. Acad. Sci. U.S.A., 69, p. 1838, 1972; W. K. Van Beek et al., Supra; and L. Hunt and S. E. Wright, Biochem. J. 229, p. 481, 1985). Increased branching may also contribute to the transformation related increase in sialic acid (K. Yamashita et al., J. Biol. Chem. 259, p. 10834, 1984; M. Pierce and Arango J., J. Biol. Chem. Cancer Res. 44, p. 3730, 1984). Branching of complex Asn-linked oligosaccharides to produce tri, tri'- and tetra-antennary structures has been associated with the action of UDP-GlcNAc: α-D-mannoside β1; 4N-acetylglucosaminyltransferase (GlcNAc transferase IV) and UDP-GlcNAc: α-D-mannoside β1,6N-acetylglucosaminyltransferase (GlcNAc transferase V) (H. Schachter, Biochem. Cell Biol. 64, p. 163, 1986 and A. Gleeson and H. Schachter, J. Biol. Chem. 258, p. 6162, 1983).

Lectins have been used as histochemical probes to study cell surface carbohydrates on tumor cells. As to the cytochemistry and histochemistry of lectins, reference may be made to the general review by DamJanov, Lab. Invest. 57, p. 1, 1987). H. Debray et al. (Int. J. Cancer, 37, p. 607, 1986) studied the expression of total cellular glycopeptides on human uroepithelial cell lines derived from transitional-cell carcinoma or from normal uroepithelium. H. Debray et al., used concanavalin A (Con A) and Lens culinaris agglutinin (LCA)- Sepharose to separate and identify the glycopeptides. U. V. Santer et al. (Cancer Res. 44, p. 3730, 1984) using immobilized lectins, Con A, leukoagglutinating phytohemagglutinin (L-PHA) and erythroagglutinating phytohemagglutinin (EPHA), reported altered glycosylation of the membrane glycoproteins of 2 different transformants generated by transfection of human DNA from cell lines with different oncogenes.

There have been a number of studies where lectin binding has been found to correlate with invasiveness and malignancy of specific tumors. C. Limas and P. Lange (Cancer 58, p. 1236, 1986) disclosed a correlation between the expression of Arachis hypogaea (peanut agglutinin) (PNA) binding sites on the surface of bladder carcinoma cells with the invasiveness and malignancy of these tumors. M. Helle & K. Krohn (Vichows Arch [A] 410 q, p. 23, 1986) found that expression of PNA receptors on breast carcinoma cells appears to be associated with the expression of estrogen receptor on these cells. However, no significant correlation has been found between PNA receptor, histologic grade and pathologic stage of tumors. (W. Böcker et al., Virchows Arch. [A] 403, p. 149, 1984 and R. A. Walker, Histopathology 9, p. 1121, 1985). Ulex europaeus agglutinin (UEA-1) has been shown to be a reliable and useful marker for endothelial cells and tumors of vascular origin (H. Holthöfer et al., Lab Invest. 47, p. 60, 1982, Am. J. Clin. Pathol. 79, p. 32, 1983, and Arch Pathol. Lab Med. 108, p. 129, 1984). Helix pomatia lectin (HPA) binding to histological sections of primary human breast carcinoma was associated with poor prognosis and short survival time (Leathem, A. J. & Brooks, S. A., Lanceti, p. 1054, 1987).

A method has been described by M. Adachi for determining tumor-associated glycolinkage (TAG) including glycoproteins, glycopeptides, glycolipids and/or sugars having an N-acetyl-D-galactosamine (AG) or L-Fucose terminus in body fluid of mammals using AG-binding lectin or L-fucose binding lectin (U.S. Pat. No. 4,455,380). Adachi has also described a method for determining TAG including glycoproteins, glycopeptides, glycolipids and/or sugars containing galactose-(β1-3 or β1-4)-N-acetylglucosamine or galactose-(β1-3 or β1-4)-N-acetylgalactosamine terminus, in body fluid of mammals using lectins which can combine specifically with galactose-(β1-3 or β1-4)-N-acetylglucosamine or galactose-(β1-3 or β1-4)-N-acetyl-galactosamine. It is disclosed in the patents that the methods can be used to detect the presence or absence of cancerous cells, to check the degree of proliferation and to determine the prosperity and decay of cancerous cells. There is no indication that the methods can be used for differentiating metastatic and non-metastatic behaviour which is of considerable importance for diagnosis and prognosis.

SUMMARY OF THE INVENTION

The present inventor has found as a result of extensive investigations that there is a direct association between expression of leukoagglutinating phytohemagglutinin (LPHA) binding β1,6-branched complex-type Asn-linked oligosaccharide and metastatic potential and that the tendency of a tumor to metastasize can be determined by reacting a tumor sample with a lectin or antibody which specifically binds to β1,6-branched complex-type Asn-linked oligosaccharide. In addition, the present inventor has found a direct association between GlcNAc transferase V activity and expression of β1,6-branched complex-type Asn-linked oligosaccharides in tissues and tumors, and therefore the tendency of a tumor to metastasize can also be determined by measuring GlcNAc transferase V activity in a tumor sample.

The capacity of tumors to metastasize is referred to as malignant potential. Malignant potential is believed to be a function of different cellular characteristics which include cell proliferation, secretion of hydrolytic enzymes for tissue invasion and cell motility.

Monosaccharide abbreviations used herein: GlcNAc=N-acetylglucosamine; GalNAc=N-acetylgalactosamine; Man=Mannose; and Gal=Galactose.

The β1,6-branched complex-type Asn-linked oligosaccharides (hereinafter referred to as BBO) include glycoproteins and glycopeptides preferably with triantennary and tetraantennary oligosaccharides, which preferably contain—GlcNAc β1-6-Man with the minimal structure

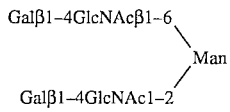

and may be larger with the structure

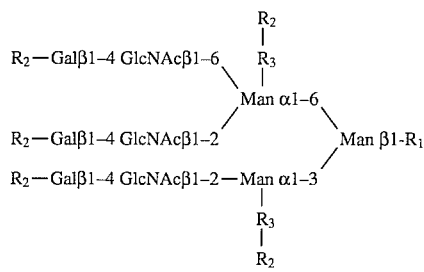

wherein $R_1$ is a synthetic linker arm or is GlcNAc β1-4 GlcNAc which may be linked to Asn or to a synthetic carrier; $R_2$ is one or more substituents, preferably sialic acid, fucose, Gal, GlcNAc, $SO_4$ and GalNAc and, $R_3$ is Galβ1-4GlcNAc linked β1-2, β1-4 or β1-6.

Broadly stated, the present invention provides a process for the determination of the malignant potential of a tumor which comprises:

(a) determining the amount of BBO in a tumor sample which comprises reacting the BBO in a tumor sample with a BBO-binding lectin or a BBO-specific antibody to form a BBO-lectin or BBO-antibody complex, and measuring the amount of the BBO-lectin or BBO-antibody complex or of unreacted BBO, or (b) determining the amount of GlcNAc transferase V activity in a tumor sample which comprises reacting the GlcNAc transferase V in a tumor sample with an acceptor substrate and a sugar nucleotide donor to produce a detectable change, and detecting the change.

In accordance with one embodiment of the invention, a process for the determination of the malignant potential of a tumor is provided which comprises reacting BBO in a tumor sample with labelled BBO-binding lectin or labelled BBO-specific antibody to form a labelled BBO-lectin or a labelled BBO-antibody complex and measuring the amount of labelled BBO-lectin or labelled BBO-antibody complex.

In accordance with another embodiment of the invention, a process for the determination of the malignant potential of a tumor is provided which comprises reacting BBO in a tumor sample with BBO-binding lectin to form a BBO-lectin complex, and measuring the amount of BBO-lectin complex using labelled BBO-binding lectin specific antibody or labelled BBO. The BBO-lectin complex may also be reacted with BBO-binding lectin specific antibody and the resulting BBO-lectin-antibody complex may be measured using antibody against BBO-binding lectin specific antibody.

In accordance with a further embodiment of the invention, a process for the determination of the malignant potential of a tumor is provided which comprises reacting BBO in a tumor sample with BBO-specific antibody to form a BBO-antibody complex and measuring the amount of BBO-antibody complex using labelled antibody against BBO-specific antibody.

The present invention also provides a competitive process or sandwiching process for the determination of the malignant potential of a tumor which comprises:

(a) competitively reacting a tumor sample and a definite quantity of insolubilized BBO with a definite quantity of labelled BBO-binding lectin or BBO-specific antibody separating the insolubilized BBO bound to labelled BBO-binding lectin or BBO-specific antibody and unbound labelled BBO-binding lectin or BBO-specific antibody from each other and measuring the labelling-agent activity of either of them;

(b) competitively reacting a tumor sample and a definite quantity of labelled BBO with a definite quantity of BBO-binding lectin or BBO-specific antibody or insolubilized BBO-binding lectin or BBO-specific antibody, separating the labelled BBO bound to BBO-binding lectin or BBO-specific antibody or insolubilized BBO-binding lectin or BBO-specific antibody and unbound labelled BBO from each other and measuring the labelling agent activity of either of them; or (c) competitively reacting a tumor sample with insolubilized BBO-binding lectin or BBO-specific antibody to form a complex of BBO and the insolubilized BBO-binding lectin or BBO-specific antibody, reacting the complex with a definite quantity of labelled BBO-binding lectin or BBO-specific antibody, separating the complex bound to the labelled BBO-binding lectin or BBO-specific antibody and unbound labelled BBO-binding lectin or BBO-specific antibody, from each other, and measuring the labelling agent activity of either of them.

The invention also broadly contemplates a diagnostic kit for the determination of the malignant potential of a tumor comprising BBO-binding lectin or BBO-specific antibody to interact with BBO in a tumor sample and means for detecting the BBO-binding lectin or BBO-specific antibody bound to BBO in the tumor sample, or unreacted BBO-binding lectin or BBO-specific antibody. A diagnostic kit for the determination of the malignant potential of a tumor comprising an acceptor substrate and sugar nucleotide donor to interact with the GlcNAc transferase V in a tumor sample to produce a detectable change and means for detecting the change in also contemplated.

BRIEF DESCRIPTION OF THE DRAWINGS

The file of this patent contains at least one drawing executed in colour. Copies of this patent with colour drawing(s) will be provided by the Patent and Trademark Office upon request and payment of the necessary fee.

DETAILED DESCRIPTION OF THE INVENTION

Figure 1:
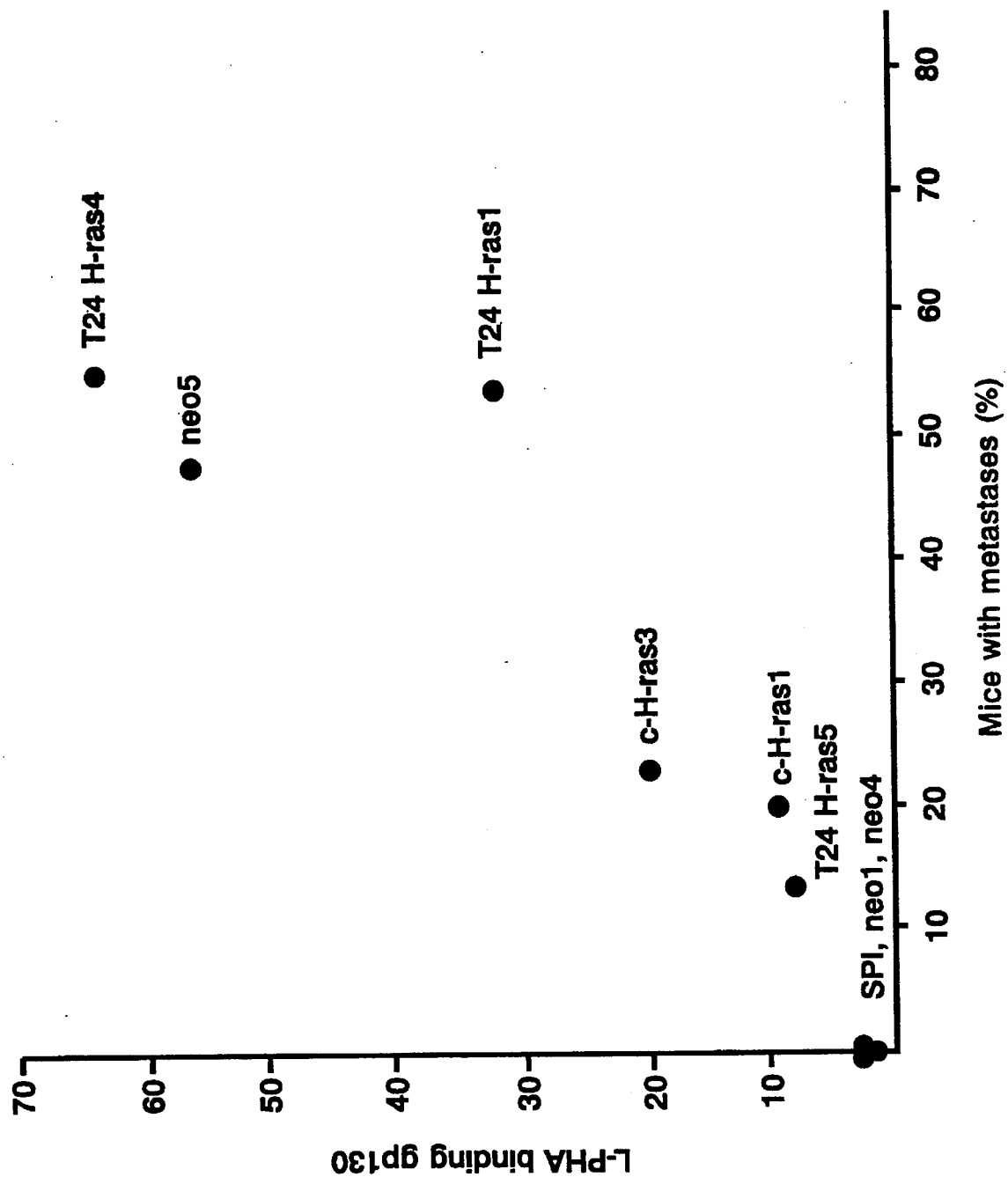
FIG. 1 is a graph showing the correlation of metastatic incidence and expression of L-PHA-binding oligosaccharides on gp130.

Tumor tissue removed from a patient can be used as the tumor sample for the determination of BBO in the process of the invention. In order to prevent tumor samples from being denatured, the samples may be stored at temperatures below −20° C. Other compounds which may be added to tumor samples are sucrose and glycerol.

A tissue section, for example, a freeze-dried or fresh frozen section of tumor tissue removed from a patient can also be used as the tumor sample for determination of BBO. The samples may be fixed and the appropriate method of fixation is chosen depending upon the type of labelling used in the process of the invention and the type of preservation of BBO. As to details relating to the general techniques of preparing tissue sections and fixation, reference may be made to general text books, for example, A. G. Everson Pearce, Histochemistry Theoretical and Applied, 4th Ed., Churchill Livingstone, Edinburgh, 1980.

A glycoprotein fraction can be separated from the tumor tissue removed from a patient and can be used as the tumor sample for the determination of BBO. Conventional methods such as precipitation, electrophoresis, affinity chromatography, gel filtration and immunoprecipitation can be used to separate out a glycoprotein fraction. More specifically the desired glycoprotein fraction can be prepared by homogenizing a tumor sample with 10 mM Tris pH 7.4, 0.9% Nacl, 2 mM PMSF 1% aprotinin, making the homogenate 0.5% tirton X-100 Tm, 0.3% sodium deoxycholate, centrifuging the lysate to remove insoluble material and separating the glycoproteins in the supernatant by SDS-polyacrylamide gel electrophoresis. The procedure for the subsequent handling of the resulting gel will depend on the type of labelling agent chosen. After electrophoretic separation of the glycoprotein fraction, the fractions may be transferred onto a membrane, for example nitrocellulose, and the membrane is probed with BBO-binding lectin or BBO-specific antibody. This procedure known as "Western" blotting is described in many text books, for example Goding, J. W., Monoclonal Antibodies: Principles and Practice, 2nd Ed., Academic Press, London, pp. 195–199, 1986.

The BBO-binding lectin of the present invention is any lectin which can combine specifically with BBO. Preferably the lectin is. LPHA or leukoagglutinin which is a tetramer of the isolectin designated L and which is derived from Phaseolus vulgaris, also known as red kidney bean. LPHA has been found to interact with galactosylated triantennary and tetraantennary glycopeptides that have at least one of the α-linked mannose residues substituted at positions C-2 and C-6 with β-linked N-acetylglucosamine (Cummings, R. D., and Kornfiled, S., J. Biol. Chem. 257, p. 11230, 1982). LPHA can be purified by the procedure of Weber et al. (Scand. J. Clin. Lab. Invest. Suppl. 24, p. 1, 1969).

BBO-specific antibody which can be used in the present invention can be polyclonal or monoclonal antibody specific for BBO. BBO-specific antibody can be prepared by conventional procedures by injecting purified BBO into a suitable host animal, (e.g. rabbit) then bleeding the animal and concentrating the antiserum. Monoclonal antibodies specific for BBO can also be prepared using the known cell fusion method. As to details relating to the preparation of monoclonal antibodies, reference can be made to Goding, J. W., Monoclonal Antibodies: Principles & Practice, 2nd Ed., Academic Press, London, p. 195, 1986.

The BBO-binding lectin or BBO-specific antibody of the present invention can be labelled with various enzymes, fluorescent materials, luminescent materials and radioactive materials. Examples of suitable enzymes include horseradish peroxidase, biotin, alkaline phosphatase, β-galactosidase, or acetylcholinesterase; examples of suitable fluorescent materials include umbelliferone, fluorescein, fluorescein isothiocyanate, rhodamine, dichlorotriazinylamine fluorescein, dansyl chloride or phycoerythrin; an example of a luminescent material includes luminol; and examples of suitable radioactive material include radioactive iodine $I^{125}$, $I^{131}$ or tritium.

The process of the invention is carried out by mixing a predetermined amount of a tumor sample with BBO-binding lectin or BBO-specific antibody or labelled BBO-binding lectin or BBO-specific antibody and incubating for 1 to 6 hours at about 4 to 20° C. The amount of BBO-binding lectin or BBO-specific antibody or labelled BBO-binding lectin or BBO-specific antibody used in the process is dependent upon the labelling agent chosen and the material to be measured. The resulting BBO-binding lectin or BBO-specific antibody bound to BBO, labelled BBO-binding lectin or BBO-specific antibody bound to BBO, or unreacted BBO-binding lectin or BBO-specific antibody or labelled BBO-binding lectin or BBO-specific antibody may be isolated by conventional isolation techniques, for example, salting out, chromatography, electrophoresis, gel filtration, fractionation, absorption, polyacrylamide gel electrophoresis, agglutination, or combinations thereof. The tumor sample or BBO-binding lectin or BBO-specific antibody may be insolubilized, for example, the tumor sample or BBO specific-antibody can be reacted using known methods with a suitable carrier. Examples of suitable carriers are Sepharose or agarose beads. When an insolubilized tumor sample or BBO-binding lectin or BBO-specific antibody is used the BBO-binding lectin or BBO-specific antibody bound to BBO or unreacted BBO-binding lectin or BBO-specific antibody is isolated by washing. For example, when the tumor sample is a glycoprotein fraction blotted onto a nitrocellulose membrane, the BBO-binding lectin or BBO-specific antibody bound to BBO or labelled BBO-binding lectin or BBO-specific antibody bound to BBO is separated from the unreacted BBO-binding lectin or BBO-specific antibody or labelled BBO-binding lectin or BBO-specific antibody by washing with a buffer, for example, phosphate buffered saline (PBS) with bovine serum albumin (BSA).

The malignant potential of the tumor sample can be calculated from the amount of the isolated BBO-binding lectin or BBO-specific antibody bound to BBO, labelled BBO-binding lectin or BBO-specific antibody bound to BBO, unreacted BBO-binding lectin or BBO-specific antibody, or labelled BBO-binding lectin or BBO-specific antibody, as measured by methods known in the art.

When labelled BBO-binding lectin or BBO-specific antibody is used, the malignant potential can be determined by measuring the amount of labelled BBO-binding lectin or BBO-specific antibody bound to BBO or of the unreacted labelled BBO-binding lectin or BBO-specific antibody. The appropriate method of measuring the labelled material is dependent upon the labelling agent. For example, if the labelling agent is an enzyme, the malignant potential can be determined by measuring the enzymatic activity using a proper enzyme substrate for colorimetric, luminescent or fluorescent systems. If the labelling agent is a fluorescent material, malignant potential can be determined by measuring fluorescence intensity, and if the labelling agent is a radioactive material, the metastatic potential can be determined by measuring the radioactivity.

When BBO-binding lectin or BBO-specific antibody is used, the malignant potential can be determined by measuring the amount of BBO-binding lectin or BBO-specific antibody bound to BBO using substances that interact specifically with BBO-binding lectin or BBO-specific antibody to cause agglutination or precipitation. In particular, when BBO-binding lectin is used, labelled BBO-binding lectin specific antibody, or, BBO-binding lectin specific antibody and labelled antibody against BBO-binding lectin specific antibody, can be added to the reaction mixture. When BBO-specific antibody is used, labelled antibody against BBO-specific antibody can be added to the reaction mixture. The malignant potential can be measured by a suitable method from among the already described techniques depending on the type of labelling agent. The BBO-binding lectin specific antibody, antibody against BBO-binding lectin specific antibody, and antibody against BBO specific antibody can be prepared and labelled by conventional procedures known in the art which have been described herein for BBO-specific antibody. The antibody against BBO-binding lectin specific antibody or antibody against BBO-specific antibody may be a species specific anti-immunoglobulin antibody or monoclonal antibody, for example, goat anti-rabbit antibody may be used to detect rabbit anti-BBO-binding lectin antibody or rabbit anti-BBO specific antibody.

In a preferred process of the invention, the malignant potential of a tumor sample is determined by measuring the amount of BBO-binding lectin bound to BBO using BBO-binding lectin specific antibody and biotinylated antibody against BBO-binding lectin specific antibody. The details of the biotinylation procedure are described more fully in Zuo-Rong S., Et al., J. Histo. Chem. Cytochem. 36:317, 1988.

An example of another substance that interacts specifically with BBO-binding lectin and can be used to measure the amount of BBO-binding lectin bound to BBO is labelled BBO. The labelled BBO is preferably a labelled oligosaccharide of a glycopeptide or glycoprotein either synthetic or naturally occurring, for example, bovine thyroglobulin or glycoprotein extracts from mouse intestinal tissues. The BBO can be labelled with enzymes, fluorescent material or radioactive materials by methods conventionally known in the art.

The amount of BBO-binding lectin bound to BBO can also be determined by measuring the amount of unreacted BBO-binding lectin using a lymphocyte proliferation assay. (Hammarstom S. et al, Proc. Natl. Acad. Sci. U.S.A., 79, p. 1611, 1982). For example, unreacted BBO-binding lectin is added to lymphocyte cultures in the presence of $^3$H-thymidine to measure mitogenic activity. After 1 to 5 days the stimulation of incorporation of $^3$H-thymidine into DNA is quantitated and compared to a standard curve produced with titred amounts of BBO-binding lectin.

The process of the present invention can also be carried out by means of a competitive or sandwiching process as described below.

1) A tumor sample and a definite quantity of an insolubilized BBO is reacted competitively with labelled BBO-binding lectin or BBO-specific antibody for about ½ to 24 hours at about 4 to 37° C., the insolubilized BBO bound to labelled BBO-binding lectin or BBO-specific antibody is separated from the unbound labelled BBO-binding lectin or BBO-specific antibody and the activity of the labelling agent on either of the materials is measured to determine the malignant potential.

2) A tumor sample and a definite quantity of labelled BBO is reacted competitively with a definite quantity of BBO-binding lectin or BBO-specific antibody or insolubilized BBO-binding lectin or BBO-specific antibody for about ½ to 24 hours at about 4 to 37° C., the labelled BBO bound to BBO-binding lectin or BBO-specific antibody or insolubilized BBO-binding lectin or BBO-specific antibody is separated from the unbound labelled BBO-binding lectin or BBO-specific antibody and the activity of the labelling agent on either of the materials is measured to determine malignant potential.

3) A tumor sample is reacted for about ½ to 24 hours at about 4 to 37° C. with insolubilized BBO-binding lectin or BBO-specific antibody to form a complex of BBO-lectin or BBO-antibody, and the complex is reacted for about ½ to 24 hours at about 4 to 37° C. with a definite quantity of labelled BBO-binding lectin or BBO-specific antibody, and the complex bound to the labelled BBO-binding lectin or BBO-specific antibody is separated from the unbound labelled BBO-binding lectin or BBO-specific antibody, and the activity of the labelling agent on either of the materials is measured to determine the malignant potential.

The insolubilized BBO and the insolubilized BBO-binding lectin or BBO-specific antibody can be prepared by reacting the material with a suitable insoluble carrier using known chemical or physical methods, for example, cyanogen bromide coupling. Examples of suitable insoluble carriers are cellulose, dextran, Sephadex, Sepharose, carboxymethyl cellulose polystyrene, filter paper, ion-exchange resin, plastic film, plastic tube, glass beads, polyamine-methyl vinyl-ether-maleic acid copolymer, amino acid copolymer, ethylene-maleic acid copolymer, nylon, silk, etc. The carrier may be in the shape of, for example, a tube, test plate, beads, disc, sphere etc.

Radioactive labelled BBO, BBO-binding lectin, BBO-specific antibody, BBO-binding lectin specific antibody, antibody against BBO-binding lectin specific antibody or antibody against BBO-specific antibody can be prepared by radiolabelling with $^{125}$I by the chloramine-T method (Greenwood et al, Biochem. J. 89:114, 1963), the lactoperoxidase method (Marchalonis et al, Biochem. J. 124:921, 1971), the Bolton-Hunter method (Bolton and Hunter, Biochem. J. 133:529, 1973 and Bolton Review 18, Amersham International Limited, Buckinghamshire, England, 1977), the iodogen method (Fraker and Speck, Biochem. Biophys. Res. Commun. 80:849, 1978), the Iodo-beads method (Markwell Anal. Biochem. 125:427, 1982) or with tritium by reductive methylation (Tack et al., J. Biol. Chem. 255:8842, 1980). For example, iodination is conducted in a suitable buffer (phosphate-buffered saline, preferably 10 mM sodium phosphate pH 7.5, 0.15M NaCl or PBS) at about room temperature using approximately 50 Ci $^{125}$I-labelled Bolton-Hunter reagent. The iodinated material is separated from the free iodine using Biogel P10 (Pharmacia).

Known coupling methods (for example Wilson and Nakane, in "Immunofluorescence and Related Staining Techniques", W. Knapp et al, eds, p. 215, Elsevier/North-Holland, Amsterdam & New York, 1978; P. Tijssen and E. Kurstak, Anal. Biochem. 136:451, 1984) can be used to prepare enzyme labelled BBO, BBO-binding lectin, BBO-specific antibody, BBO-binding lectin specific antibody, antibody against BBO-binding lectin specific antibody, and antibody against BBO-specific antibody.

Fluorescent labelled BBO, BBO-binding lectin, BBO-specific antibody, antibody against BBO-binding lectin specific antibody, and antibody against BBO-specific antibody can be prepared by reacting the material with umbelliferone, fluorescein, fluorescein isothiocyanate, dichlorotriazinylamine fluorescein, dansyl chloride, derivatives of rhodamine such as tetramethyl rhodamine isothiocyanate, or phycoerythrin.

In the process of the invention for the determination of GlcNAc transferase V activity in a tumor sample, the acceptor substrate may be an oligosaccharide, a glycopeptide or a glycoprotein either synthetic with linkers at the reducing end or naturally occurring structures, for example, asialo-agalacto-fetuin glycopeptide. Minimal structure for the oligosaccharide portion may be GlcNAc β1-2 Man α1-6Man-$R_1$, wherein $R_1$ is GlcNAc β1-4GlcNAc with or without fucose, or a synthetic linker or derivatives of GlcNAc β1-2 Man β1-6 Man-$R_1$ , for example, derivatives where hydroxyl(s) are removed or substituted by, for example, halogen or phenol. A preferred naturally occurring structure is GlcNAc 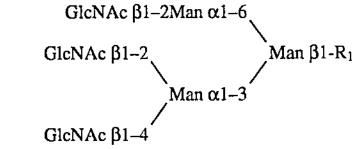 wherein $R_1$ is as defined above. The sugar nucleotide donor is uridine diphospho-N-acetylglucosamine (UDP-GlcNAc) which can be labelled in the GlcNAc portion with radioactive groups or other nonradioactive groups which can be used for product detection. The concentration of the acceptor substrate and of the labelled UDP-GlcNAc in the reaction may range from 0.01 mM to 10 mM and the duration of the reaction from 5 minutes to 24 hours.

The GlcNAc transferase V in a tumor sample is reacted with the substrate and sugar donor at a pH and temperature effective for the GlcNAc transferase V to interact with the substrate and produce a detectable change corresponding to the presence and/or concentration of the enzyme. The substrate and sugar donor are effective to interact with the GlcNAc transferase V within wide pH and temperature ranges, for example from about 5 to 8 and from about 30 to 45° C., preferably from 37° C.

It is preferred to use a buffer with the acceptor substrate and sugar donor. The buffer and substrates together can be used as an assay composition. A buffer is present in such a composition to maintain the pH within the pH range effective for GlcNAc transferase V. Other compounds such as EDTA and detergents may be added to the assay composition.

A cell lysate fraction can be separated from a tumor sample removed from a patient and can be used as a tumor sample for the determination of GlcNAc transferase V activity. Conventional methods can be used to separate out a cell lysate fraction. More specifically, the desired cell lysate fraction can be prepared by suspending the tumor sample in 10 mM Tris-HCl pH 7.4, 0.9% NaCl, 1 mM PMSF and 0.1% aprotinin homogenized using a Polytron homogenizer. After centrifugation the membrane pellet may be solubilized in 1% Triton X-100™, 40 mM sodium cacodylate, pH 7.0 and nuclei and debris may be removed by centrifugation.

The detectable change produced by the interaction of GlcNAc transferase V with the substrate and sugar nucleotide donor may be colorimetric, photometric, radiometric, potentiometric, etc. Accordingly, the detectable change can be detected by a wide variety of means. For example, the process can employ a suitable detection device capable of detecting a change in absorption density, a change in fluorescent or radioactive emission or a shift in the absorbance of a characteristic λ max. The detectable change can also be measured by reacting with a labelled antibody specific for the minimal structure features of the product, in particular the following minimal structure features of the product:

This product may be further galactosylated at about 4° to 45° in a subsequent 5 minute to 24 hour reaction using UDP-Gal at 0.01 to 10 mM concentration and Bovine galactosyltransferase at 1 to 1000 μml U per nMole of acceptor substrate to produce the BBO structure which can be detected with a BBO specific lectin or antibody.

GlcNAc transferase V activity may also be determined using methods based on HPLC (Koenderman et al., FEBS Lett. 222:42, 1987) or methods employing synthetic oligosaccharide acceptors attached to hydrophobic aglycones (Palcic et al, GlycoconJugate 5:49, 1988 and Pierce et al, Biochem. Biophys. Res. Comm. 146:p. 679, 1987).

The process of the invention can be carried out using a diagnostic kit for determining malignant potential of tumor cells in a tumor sample. The kit contains labelled or unlabelled UDP-GlcNAc, and acceptor substrate. For kits with unlabelled UDP-GlcNAc the kit also contains UDP-Gal, galactosyltransferase BBO-specific antibody or BBO-binding lectin to interact with BBO in the sample. The kit also contains means for detecting the BBO-binding lectin or BBO-specific antibody bound to BBO or unreacted BBO-binding lectin or BBO-specific antibody. Labelled BBO-binding lectin or BBO-specific antibody and means for detecting the labelling may be used in the diagnostic kit. Alternatively, labelled antibody against BBO-binding lectin or BBO-specific antibody can be used in the kit. Competitive methods using insolubilized BBO and labelled BBO-binding lectin or BBO specific-antibody; labelled BBO and BBO-binding lectin or BBO-specific antibody; or, insolubilized BBO-binding lectin or BBO-specific antibody, labelled BBO-binding lectin or BBO-specific antibody and labelled BBO-binding lectin or BBO-specific antibody, may also be employed in the diagnostic kit.

Suitable detecting means used in the kit include the use of colorimetric spectrophotometry, fluorescence spectrophotometry, radiometry, chemiluminescence, enzyme labelling, and the like. This applies to kits containing either labelled GlcNAc for direct product detection, or unlabelled UDP-GlcNAc for detection of galactosylated product (i.e. BBO).

Preservatives and/or stabilizers such as bovine serum albumin antibacterial agents such as $NaN_3$ may be added to the BBO-binding lectin or BBO specific antibody used in the kit. The BBO binding lectin or antibody in the kit may be a freeze-dried product and the kit may contain a water-soluble or water-miscible solvent. Examples of suitable solvents are water and PBS. The kit may additionally contain a buffer solution, preferably a buffer solution having a pH of from 6 to 8. The amount of BBO-binding reagent contained in the kit is chosen appropriately depending upon the type of labelling agent or the material to be measured. Preferably, the BBO binding lectin or BBO-specific antibody is contained in an amount of from 0.01 µg/ml to 5.0 mg/ml.

The kit may comprise labelled UDP-GlcNAc and an acceptor substrate to interact with GlcNAc transferase V in the sample to produce a detectable change and means for detecting the change. Suitable acceptor substrates and detecting means for detecting the change produced by the interaction of GlcNAc transferase V with the substrate and sugar nucleotide donor are described above.

The process of the invention can be used for determining the malignant potential of a wide range of tumors including carcinomas, sarcomas, lymphoid tumors, neuronal tumors, in particular fibroadenomas, ductal hyperplasia, adenocarcinomas, colorectal carcinomas, malignant melanomas and cancers of tissue not included in these common groups.

The following examples below illustrate the invention.

The following information is common to the examples:
Cell Lines

The origin of the highly metastatic DBA/2 mouse tumor called MDAY-D2 and selection of lectin-resistant mutants of MDAY-D2 is described in Kerbel, Am. J. Path 97, p. 609, 1979 and Dennis et al, Nature (Lond.) 292, p. 242, 1981. SP1 is a mouse mammary carcinoma which arose spontaneously in a retired CBA/3 breeder. The cell lines were routinely grown in antibiotic-free alpha-MEM medium containing 7% fetal calf serum (FCS). The cell lines were shown to be free of mycoplasma as detected by staining with Hoechst 33258.

SDS—Polyacrylamide Gel Electrophoresis

SDS-polyacrylamide gel electrophoresis was performed on 12.5% resolving gels under reducing conditions with 40 µg of protein per lane. Gels were fixed and stained in water/acetic acid/methanol (5/1/5 v/v), 0.25% Coomassie brilliant blue R250. The gels were incubated with iodinated lectins for 16 hours, washed exhaustively over a 3-day period, dried and exposed to x-ray film at −70° C. for 1.5 days.

Protein Iodination

Wheat germ agglutinin (WGA) (Sigma) was iodinated with 500 µCi of $Na^{125}I$ and Iodogen beads (Pierce) in 0.5 ml of phosphate-buffered saline (PBS), pH 7.0. L-PHA (Pharmacia) was iodinated with 500 µCi of $^{125}I$-labelled Bolton-Hunter reagent. Prior to incubating with the gels fixed and stained with Coomassie brilliant blue, the iodinated lectins were passed over a P10 column (1 by 30 cm) equilibrated in sodium phosphate, pH 6.8, 0.2M NaCl, 1 mM $CaCl_2$, 1 mM MgCl2, and 0.02 mM $NaN_3$.

EXAMPLE 1

Lectin Sensitivity and Malignant Potential of Class 3 Lectin Mutants.

Class 3 glycosylation mutants were selected from $10^7$ MDAY-D2 cells plated in alpha minimal essential medium plus 7% FCS with 50 µg/ml of L-PHA and 20 µg per milliliter of BSII lectin from *Bandeirea simplicifolia*. The two surviving colonies were subcloned and one clone of each, termed KBL1 and KBL2, were tested for lectin sensitivity. Tumor cell proliferation in the presence of increasing concentrations of lectin was determined by measuring $[^3H]$ thymidine for 4 hours and the lectin concentration that reduced the isotope incorporation to 50% of the control was determined (D50). The ratio of mutant to wild-type D50 values for L-PHA ranged between 4 and 5 in five independent experiments. Tumorigenicity or the number of cells required for 50% tumor take was assessed by injecting 10, 50, $10^2$ and $10^3$ cells subcutaneously into syngeneic DBA/2J mice (five mice per group). Spontaneous liver metastases were counted by visual inspection of the liver of mice that had been injected subcutaneously with $10^5$ tumor cells. The mice were examined on day 38 and organs were minced and placed in tissue culture. Only three liver nodules were found in mice injected with class 3 cells and no tumor cells grew out from the organ cultures of livers that had no visible nodules.

TABLE I

| Cell Line | Lectin sensitivity (D50, µg/ml) | | | | Tumorigenicity | Spontaneous Liver metastases |
|---|---|---|---|---|---|---|
| | L-PHA | WGA | Con A | BSII | (cell number) | (nodules/liver) |
| MDAY-2 | 5 | 6 | 35 | >50 | 50 to 100 | 15, >100, >100, >100, >100, >100 |
| KBL1 | 25 | 6 | 25 | >50 | 10 to 50 | 0, 0, 0, 0, 0, 0, 0, 0, 0 |
| KBL2 | 25 | 6 | 25 | >50 | 50 to 100 | 0, 0, 0, 0, 0, 1, 1, 1 |

As shown in Table I, the two clones KBL1 and KBL2 with identical lectin sensitivity profiles were isolated, and although the mutants were highly tumorigenic, their metastatic potential was dramatically reduced. Compared to MDAY-D2, the mutants were poorly metastatic when injected by either intravenous or subcutaneous routes.

EXAMPLE 2

Characterization of the Oligosaccharide Defect Class 3 Cells.

Plasma membrane fractions were purified from MDAY-D2 and KBL1 cells and glycoproteins were separated by SDS-polyacrylamide gel electrophoresis. The gels were incubated with $^{125}I$-labelled WGA or L-PHA for 16 hours and then washed exhaustively over a 3-day period, dried, and exposed to x-ray film at −70° C. for 1.5 days.

The class 3 mutant KBL1 showed a loss of L-PHA binding to cell surface glycoprotein gp 130 but no change in wheat germ agglutinin binding. The lack of change in the latter suggests the presence of sialic acid, since removal of this residue with neuraminidase eliminates WGA binding (Dennis et al., J. Cell. Biol. 99:1034, 1984). Loss of L-PHA binding indicates a decrease in 1–6 branched complex-type oligosaccharides in class 3 cells.

Cell-surface sialic acid residues were also labelled by exposure to sodium periodate and tritiated sodium borohydride. Specifically, MDAY-2 and KBL1 cells ($5 \times 10^6$ per milliliter) in PBS were placed on ice and 25 µl of 0.08 $NaIO_4$ was added and left to react for 10 minutes. The cells were washed three times in PBS and 250 µCi of $NaB^3H_4$ was added. After 20 minutes the cells were washed three times in PBS, then 100 µg of carrier beef brain gangliosides (Supelco, Inc., Oakville, Ontario) was added and the cells were extracted in 50 ml of a mixture of chloroform and methanol (2:1, v/v). Folch partitioning was used to separate glycolipids into neutral and acidic fractions, corresponding to lower and upper phases, respectively. Fractions were analyzed by high-performance thin-layer chromatography (HPTLC) and developed in chloroform, methanol, and 0.02% $CaCl_2$ (60:40:9, v/v), respectively, and then plates were sprayed with En$^3$hance exposed to Kodak XAR x-ray film for 1 week.

The results confirmed that the cell surface glycoprotein gp130 was sialylated to a similar degree in the class 3 mutant and wild-type cells. Since the mutant cells retained sialylated complex-type oligosaccharides but no longer bound L-PHA, it appeared that the defect might be restricted to the addition of the β1-6 antennae.

EXAMPLE 3

GlcNAc-Transferase Activities in Cell Lysates of MDAY-D2 and Class 3 Mutant Cells Grown in Tissue Culture.

GlcNAc-transferase V activity, the enzyme that initiates β1-6 linked antennae as well as GlcNAc-transferase IV and I, were compared in cell lysates of mutant and wild-type cells. MDAY-D2 and class 3 mutant cells (approximately 50×10$^6$) were suspended in 0.2 NaCl and lysed by freeze-thawing. The particulate fraction was washed three times with saline. After centrifugation the membrane pellet was solubilized in 200 µl of 1% Triton X-100™, 40 mM cacodylate, pH 7.0 and centrifuged at 2000 g to remove nuclei and debris. The reaction mixture contained 12 nmol of UDP-(3H) GlcNAc (60,000 cpm/nmol), 0.125 mM GlcNAc, 20 nmol of glycopeptide substrate, ovalbumin glycopeptides GlcNAc$_2$ Man$_3$-GlcNAc$_2$-Asn (transferases IV and V) and Man$_5$GlcNAc$_2$-Asn (transferase I), and 2 mM $MnCl_2$ for transferase I and IV+V or 20 mM Na$_2$EDTA for transferase V in a final reaction volume of 40 µl. Half the reaction volume was cell lysate containing 30 to 100 µg of protein, and after 1 hour of incubation at 37° C., the reaction mixture was passed over a Dowex AG1-X8 column and the excluded material was spotted on paper and washed in 80% ethanol by descending paper chromatography. Product was eluted from the paper and counted to produce the data shown in Table II. To test for triantennary product, transferase IV+V and V products were applied to ConA sepharose and found to be 70 to 80% and 100% excluded, respectively. The data in Table II show the mean of duplicates ±SEM.

TABLE II

| Cell Line | GlcNAc transferase activity (nmol/mg per hour) | | |
|---|---|---|---|
| | IV + V | V | I |
| MDAY-D2 | 0.40 ± 0.02 | 0.023 ± 0.002 | 2.70 ± 0.1 |
| KBL1 | 0.14 ± 0.01 | 0.048 ± 0.003 | 5.77 ± 0.02 |

The class 3 mutant KBL1 showed 20% and 60% of the wild-type levels of transferase V and IV activities, respectively, and a twofold increase in transferase I activity (Table II). This is consistent with the loss of L-PHA binding oligosaccharides; however, the coordinate change in the activity of GlcNAc transferases IV and I suggests that the mutation may affect a regulatory mechanism for a number of the GlcNAc transferases. The decreased levels of transferases V and IV would be expected to increase the proportion of biantennary complex-type oligosaccharides and this could explain the increased ConA sensitivity of the class 3 cells (Table I).

EXAMPLE 4

To determine whether enhanced expression of the L-PHA binding oligosaccharides in nonmetastatic or immortalized cell lines may be associated with acquisition of metastatic potential, the metastatic phenotype in rat 1 fibroblasts and the nonmetastatic mouse mammary carcinoma called SP1 was induced by transfecting the lines with the entire 7.0-kb v-K-ras oncogene ligated into EcoRI site of pBR322(t). (Muschel et al., Am. J. Pathol. 121, p. 1, 1985; Pozzatti et al., Science, 232, p. 223, 1986; Bradley et al., Proc. Natl. Acad. Sci. USA, 83, p. 5277, 1986; Johnson et al., J. Exp. Med. 162, p. 1732, 1986)). v-K-ras transfected rat 1 cells injected subcutaneously into BALB/c nude mice produced tumors, and metastases were found in the kidneys and lungs of the tumor-bearing mice. The plasma membrane glycoproteins of the v-K-ras transformed cells were separated by SDS-gel electrophoresis and stained by direct overlay with $^{125}$I-labelled wheat germ agglutinin (WGA) and L-PHA. The v-K-ras transformed cells showed a large increase in L-PHA binding to a 130-kD glycoprotein but no change in the intensity of WGA staining in this region of the gel. It appears that the previously observed increase in β1-6 branching of complex-type oligosaccharides in v-K-ras transfected cells (Santer et al., Cancer Res. 44, p. 3730, 1984) is heavily represented on gp130.

EXAMPLE 5

Correlation of Metastatic Incidents a Ad L-PHA Binding.

To segregate the tumorigenic and metastatic phenotypes, experiments were conducted in the tumorigenic but nonmetastatic mammary adenocarcinoma line called SP1. The cells were transfected with either pSV$_2$neo (neomycin resistance) alone or with pSV$_2$neo linked to activated T24Hras oncogene or nonactivated c-H-ras. G418 resistant clones were selected and then tested for the expression of the transfected genes, spontaneous metastasis in syngeneic CBA/J mice, and expression of the L-PHA binding gp130.

Cell lysates from cloned SP1 lines transfected with pSV$_2$neo, pSV zneo·c·H-ras or pSV$_2$neo·T24 4H-ras were separated by SDS-gel electrophoresis, electroeluted onto nitrocellulose paper, and blotted with $^{125}$I-labelled WGA and L-PHA.

FIG. 1 is a graph showing the correlation of metastatic incidence and expression of L-PHA-binding oligosaccharides on gp130. The intensity of L-PHA-staining gp130 in SP1 cells and cloned transfectant lines were plotted against the metastatic incidence (that is, number of mice with visible metastases out of numbers of mice injected). The clones were injected subcutaneously into syngeneic CBA/J mice as well as BALB/c nude mice (15 mice per cloned cell line). Metastatic nodules were found in the lungs, and no difference in incidence between CBA/J and nude mice was observed.

Although some metastatic clones were obtained after transfection with pSV$_2$neo alone and pSV$_2$neo·c·H-ras (10 to 20%), there was a significant increase in the proportion of metastatic clones obtained from the pSV$_2$neo·T24H-ras transfected cells (100%). (Kerbel et al., Proc. Natl. Acad. Sci. USA, 84, p. 1263, 1987, and Waghorne et al, Oncogene 1, p. 149, 1987). Most significantly the intensity of L-PHA binding to gp130 showed a strong positive correlation with metastatic propensity, regardless of the plasmid constructs that had been introduced into the cells.

EXAMPLE 6

In a population of tumor cells heterogeneous for the metastatic phenotype, the subpopulation of cells with high levels of L-PHA binding sites on gp130 would be expected to undergo selective metastasis. To test this, a. pool of pSV$_2$neo transfected SP1 cells (50 to 100 clones), which would be expected to have a minor subpopulation of metastatic cells was injected subcutaneously into syngeneic mice. Forty days later 100% of the animals had visible metastasis in either lungs or kidneys. Tumor cells obtained from metastatic nodules and established in tissue culture showed elevated levels of L-PHA binding gp130 compared to the injected cells, indicating that the tumor cell with increased β1-6 branching had a selective metastatic advantage over the majority of the cells which expressed low levels of L-PHA-binding gp130.

EXAMPLE 7

L-PHA Reactivity and GlcNAc-Transferase V Activity in Mouse Tissue.

The increased levels of β1-6 branched Asn-linked oligosaccharides in fibroblast lines transfected with polyoma virus appears to be due to a 2–5 fold increase in GlcNAc-transferase activity (Yamashita et al., J. Biol. Chem. 260, 3963, 1985). Other GlcNAc transferase activities were not altered suggesting that expression of β1-6 antenna may be developmentally regulated by controlling GlcNAc-transferase V activity.

L-PHA staining density in normal mouse tissue

Serial dilutions of tissue lysates were separated by SDS-PAGE, transferred to nitrocellulose and blotted for L-PHA reactive structures. Relative L-PHA staining was quantitated by densetometer scanning of the blots.

Preparation of mouse tissues

DBA/2 mouse organs were removed, rinsed in ice-cold PBS and immediately frozen in liquid nitrogen. Human breast biopsies were stored at –70° C. within 20 minutes of being removed from the patients then crushed with a mortar and pestle at –70° C. The mouse and human tissues were homogenized in a Polytron homogenizer in 2–5 ml of 50 mM Tris-HCl pH 7.5, 0.15M NaCl, 2 mM PMSF, 1 mM aprotinin. The mouse tissues were centrifuged at 20,000× g for 30 minutes and the pellets extracted as above for both the SDS-PAGE and glycosyltransferase assays.

Lectin Blotting

The proteins separated by 12% SDS PAGE under reducing conditions were transferred electrophoretically onto nitrocellulose sheets in buffer consisting of 25 mM Tris, 0.2M glycine which contained 20% methanol. Blots were blocked for 1 hour at 37° C. in 50 mM Tris-HCl pH 8.0, 0.15M NaCl (TBS), 5% BSA for L-PHA blots. The blots were incubated for 1 hour with L-PHA or PNA or WGA (0.1 g/ml) in PBS/0.1% BSA. Following three 5 minute washes in PBS/0.1% BSA, lectin blots were incubated for 1 hour with a 1/1000 dilution of rabbit anti-lectin antibody in TBS, 0.1% BSA. Immunoblots and lectin blots were subjected to three 5 minute washes in TBS, 0.1% BSA and incubated for 1 hour in alkaline phosphatase coupled goat anti-rabbit antibody diluted 1/3000 in TBS, 0.1% BSA. Blots were washed 4 times (5 minutes each) followed by one wash in TBS, 0.05% Tween 20 and one wash in TBS. The blots were developed according to manufacturer's instructions (Bio Rad).

Figure 2:
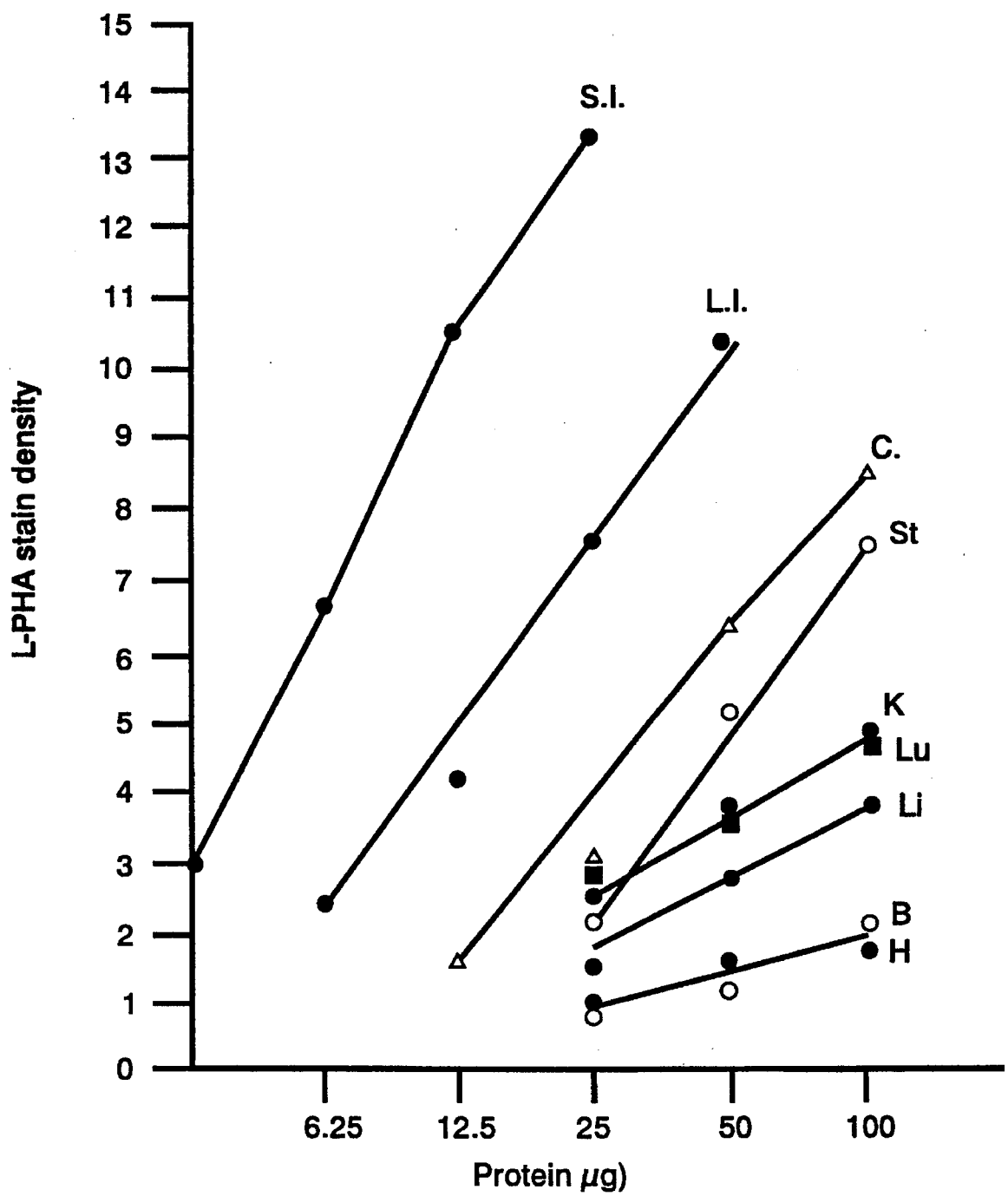
FIG. 2 is a graph showing L-PHA activity in human breast biopsies and DBA/2 mouse organs.

FIG. 2 shows that L-PHA reactive structures are not restricted to transformed cells but appear to be expressed in a tissue specific manner in the mouse. In the Figure the following abbreviations are used: S.I.-Small Intestine; L.I.-Large Intestine; C-Colon; St-Stomach; K-Kidney; Lu-Lung; L-Liver; B-Brain; H-Heart.

EXAMPLE 8

GlcNAc-Transferase Activity in Mouse Tissue Correlates With L-PHA Reactivity.

Method: GlcNAc-Transferase Assays

Organs from one mouse or human tumor tissue were homogenized in 10 volumes of 10 mM Tris-HCl pH 7.4, 0.9% NaCl, 1 mM PMSF and 0.1% aprotinin using a Polytron homogenizer. Following centrifugation at 20,000 g for 30 minutes, the pellet was stored at –70° C. until the day of the assay, at which point the sample was suspended in 100 mM sodium cacodylate pH 6.4, 2 mM MnCl$_2$, 0.5% Triton-X-100™. Samples were spun at 3,000×g for 10 minutes and the supernatants were used as the source of enzyme. The standard reaction contained 12 nmole of UDP-($^3$H)GlcNAc (440,000 cpm/nmole), 0.1 mM GlcNAc, 20 nmole of glycopeptide substrate, 25 µl tissue. extract containing 50–200 µg of protein and 10 mM Na$_2$EDTA for transferase V in a final reaction volume of 50 µl. In preliminary experiments, the UDP-GlcNAc and glycopeptide substrate were 5 nmoles and 10 nmoles, respectively. The glycopeptide GlcNAc$_3$Man$_3$GlcNAc$_2$-Asn was prepared from a pronase digest of fetuin and used as the substrate for transferase V. Sialic acid was removed from the glycopeptide by 0.1M HCl at 80° C. for 1 hour and galactose was removed by exhaustive digestion with jack bean β-galactosidase and bovine testicular β-galactosidase. Following a 2 hour incubation at 37° C., reaction mixtures were boiled, passed over a Dowex AGI-X8 column and the excluded material spotted on paper and washed in 80% ethanol by descending paper chromatography for 24 hours. The product was eluted from the origin and radioactivity measured in a beta counter.

Figure 3:
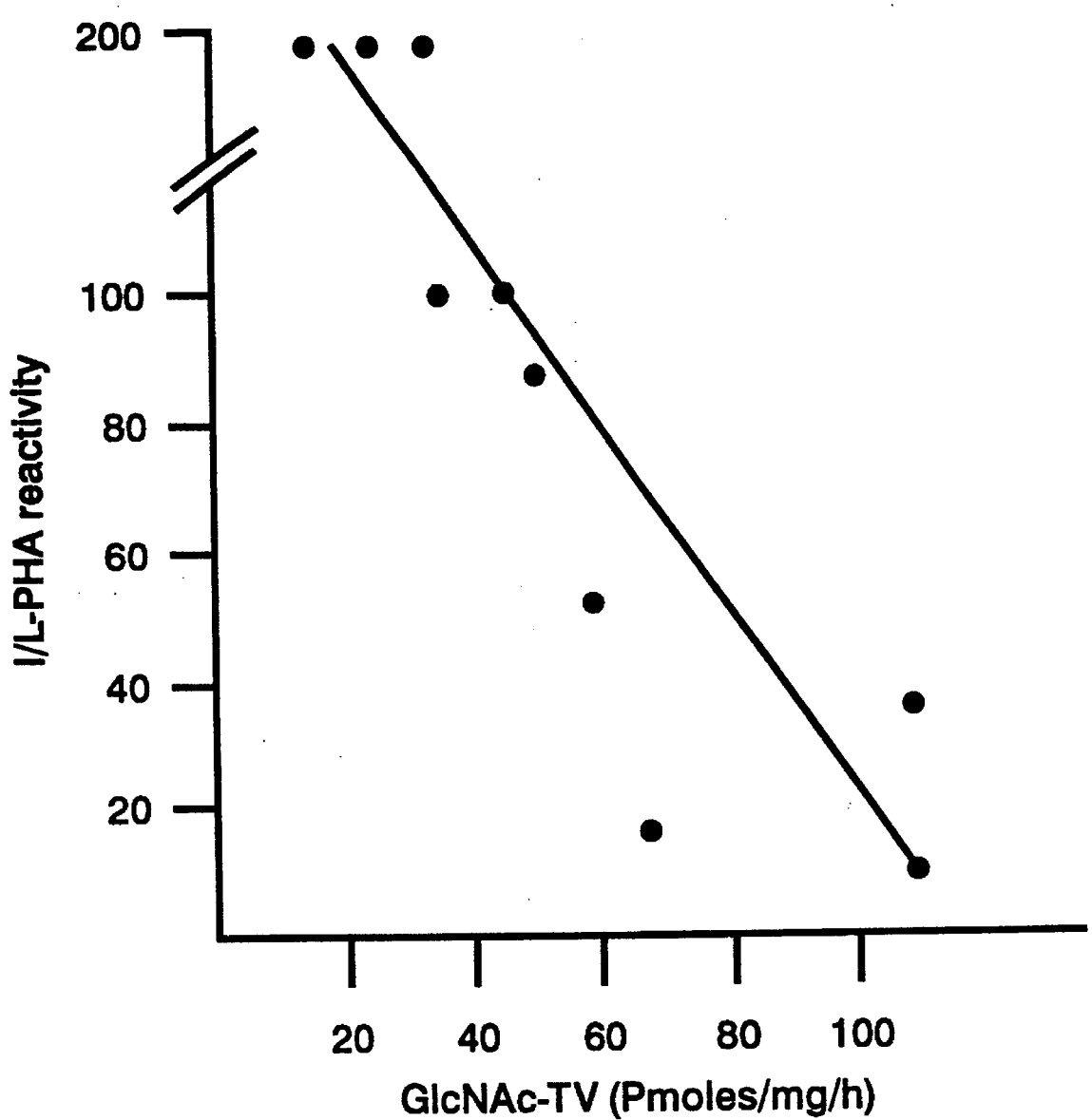
FIG. 3 is a graph showing the level of GlcNAc transferase V activity in 10 mouse tissue-homogenates as a function of 1/L-PHA staining density.

FIG. 3 shows the levels of L-PHA reactivity in the mouse tissues correlated with expression of GlcNAC-transferase V activity suggesting that the enzyme activity in tissues may also be diagnostic for the presence of β1-6 branched structures.

EXAMPLE 9

L-PHA Reactivity and GlcNAc-transferase V Activity in Human Breast Biopsies.

Samples of primary breast tissue biopsies were prepared for SDS-PAGE and lectin blotting. When sufficient amounts of tissue were made available, GlcNAc-transferase V assays were also conducted to determine enzyme activity.

The density of L-PHA staining was determined by densetometric scanning of lectin blots and expressed as a ratio of L-PHA staining density in 50 µg of mouse small intestine. Human tissue homogenates were divided in half, one aliquot was made 0.5% Triton X-100™, 0.4% sodium deoxycolate and left on ice for 1 hour. The lysate was centrifuged at 10,000×g for 5 minutes, proteins were determined using BCA reagent (Pierce) and aliquots of 100 µg were precipitated with 10 volumes of acetone at –20° C. for separation on SDS-PAGE and lectin blotting. The second aliquot was centrifuged at 20,000×g for 30 minutes and the pellet was stored at –70° C. and used for glycosyltransferase assays.

Figure 4:
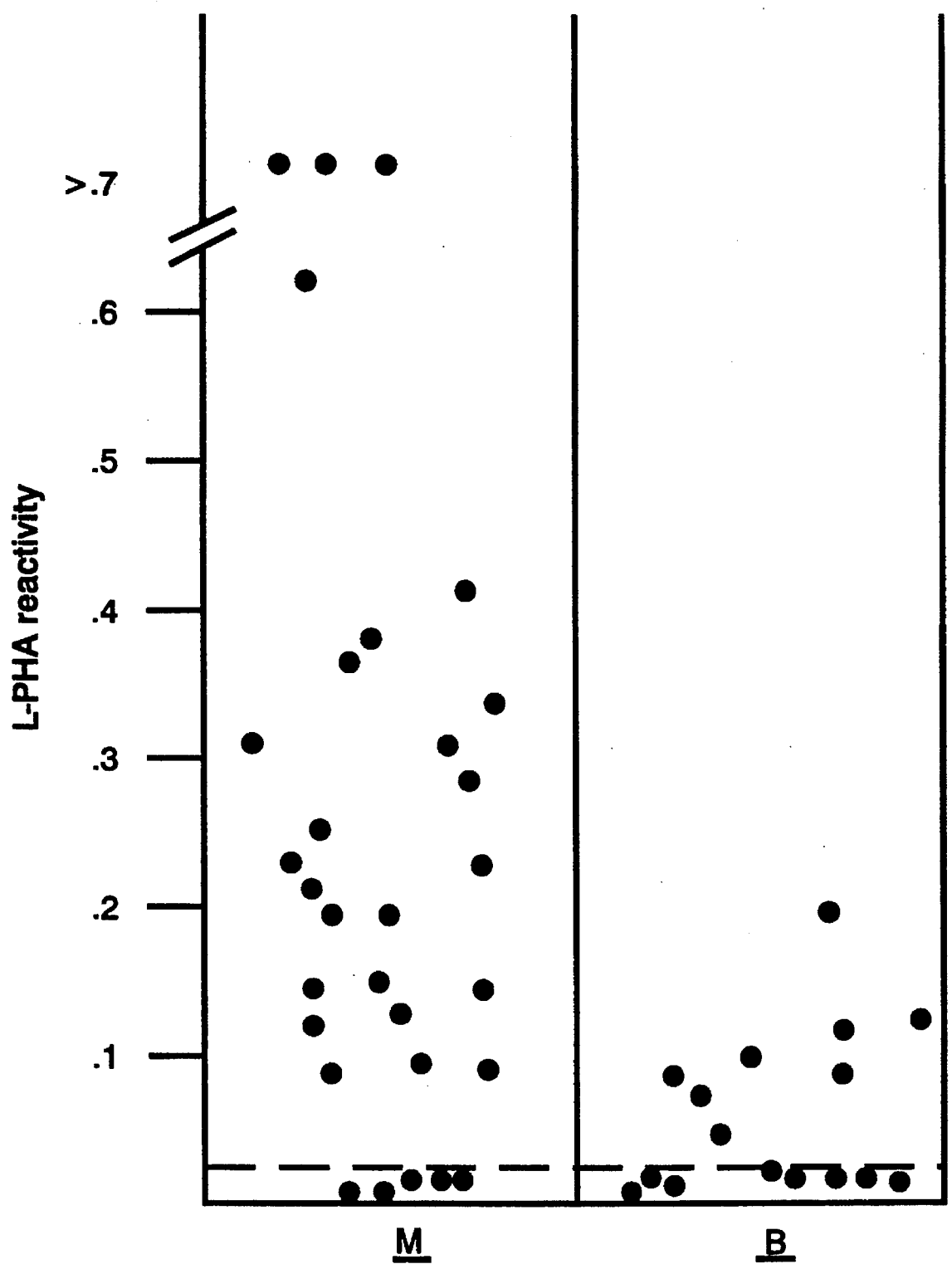
FIG. 4 is a graph showing the distribution of L-PHA staining density in lectin blots of benign and malignant breast lesions.

L-PHA binding glycoproteins were negligible in normal breast tissues and benign lesions but readily detected in some malignant samples (FIG. 4). L-PHA reactivity in benign tissues was compared to that in 50 µg of protein prepared from mouse intestine and produced a mean reactivity ±S.D. of 0.058 ±0.053. For 30 malignancies 50% were positive (i.e., more than 3 S.D. above the mean of the benign); 27% were within 2 S.D. of the mean for benign; and 23% were negative (i.e., within 1 S.D. of the mean for the benign).

EXAMPLE 10

L-PHA Reactivity Correlates with GlcNAc-transferase Activity.

Figure 5:
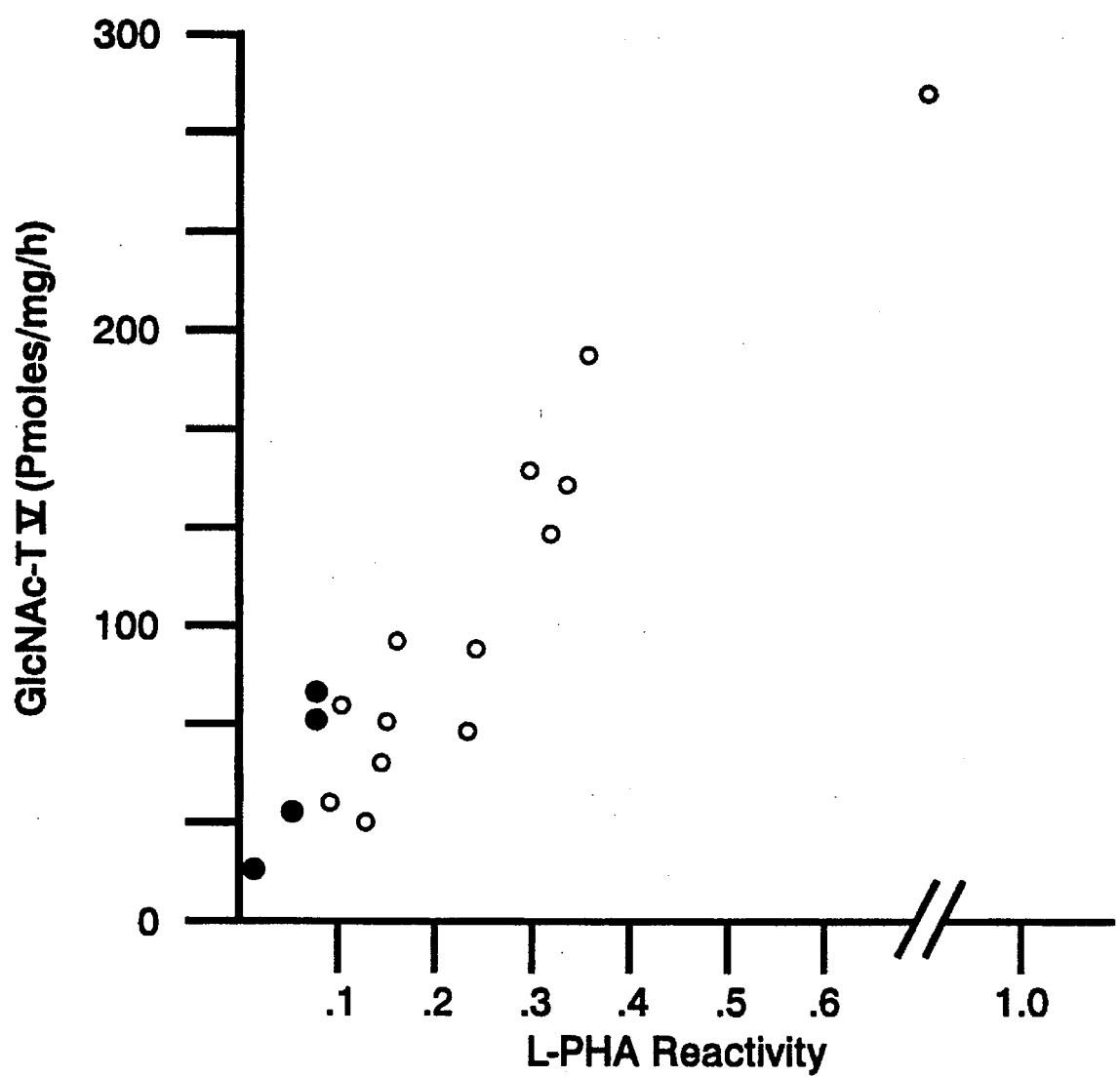
FIG. 5 is a graph showing GlcNAc transferase V activity as a function of L-PHA staining density in human breast biopsy samples.

L-PHA reactivity in 17 human breast samples correlated with GlcNAc-transferase V activity as was observed in the normal mouse tissues (FIG. 5—open circles are malignant samples and closed circles are benign samples). Therefore expression of the L-PHA reactive structures appears to be dependent on increased GlcNAc-transferase activity in the tumors.

EXAMPLE 11

Method for Detection of L-PHA Reactive Olgosaccharides in Tissue Sections by Lectin Histology.

Tissue samples were fixed in formalin, embedded in paraffin and 5 µ sections were cut and mounted on glass slides which had been pre-coated with 1% gelatin. The sections were deparaffinized with 3 washes in xylene, 5 minutes each, then rehydrated with sequential 2 minute washes in ethanol, 70% ethanol, $H_2O$ and finally 50 mM Tris HCl pH 7.5, 0.15M NaCl (TBS). The slides were soaked in 20% normal goat serum for 10 minutes to reduce nonspecific staining. The sections were then stained for L-PHA reactive oligosaccharides using L-PHA (Pharmacia), rabbit anti-L-PHA antiserum prepared in the inventor's laboratory and a streptavidin-biotin kit supplied by Zymed Labs Inc. (Ca., U.S.A.). Briefly, 2–3 drops of reagent solutions, sufficient to cover the specimens, were added and the sections were incubated in a humidified box at room temperature. The following solutions were sequentially added for the indicated times, then washed from the slides with TBS. L-PHA in TBS at 1 µg/ml for one hour; a 1/500 dilution of rabbit anti-L-PHA antiserum for one hour; then as recommended for use of the Zymed kit, two drops of biotinylated goat anti-rabbit antiserum for 10 minutes; 2 drops of a 1/100 dilution of streptavidin-peroxidase for 5 minutes; 100 µl of substrate-chromogen mixture containing aminoethylcarbazole for 15 minutes; and finally the sections were counterstained with hematoxylin and mounted using an aqueous mounting medium provided with the kit.

The slides were examined using a light microscope and scored by two independent observers as follows: 0=no staining; +=faint cytoplasmic blush or fine stippling; ++=few coarse cytoplasmic granules; +++=many coarse cytoplasmic granules or globules. The percentage of cells in each grade was estimated visually for 5–10 fields. This was done independently by two pathologists. Weighted scores were calculated for each sample by assigning weights of 4, 3, 2, and 1 to +++, ++, + and 0 respectively, summing the % of the cells×weight in each category.

EXAMPLE 12

L-PHA Reactivity in Benign and Malignant Human Breast Biopsies determined by Lectin Histology.

Figure 6A:
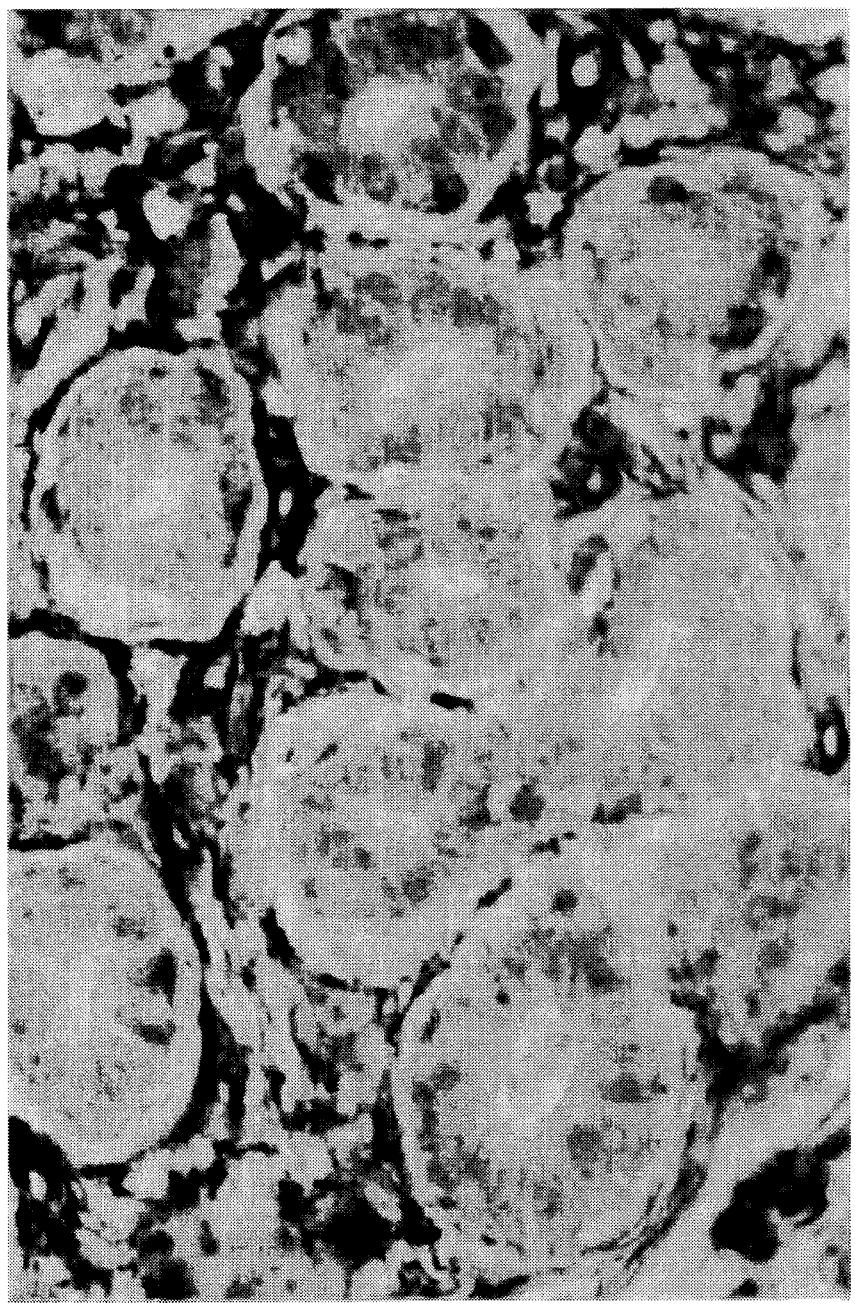
FIG. 6(A) is a photograph showing L-PHA staining in histological sections of human breast fibroadenomas.
Figure 6B:
FIG. 6(B) is a photograph showing L-PHA staining in histological sections of ductal hyperplasia.
Figure 6C:
FIG. 6(C) is a photographs showing L-PHA staining in histological sections of adenocarcinoma.

L-PHA reactive oligosaccharides were quantitated in histological sections of 18 fibroadenomas (benign), 16 ductal hyperplasia (premalignant) and 18 adenocarcinoma (malignant) using the method set out in Example 11. Staining was noted both in the cytoplasm and at the surface of tumor cells. FIG. 6 shows L-PHA histological sections of human breast Fibroadenomas (FIG. 6A), ductal hyperplasia (FIG. 6B) and a case of adenocarcinoma (FIGS. 6C). In normal and benign tissue the ductal epithelial cells showed weak to moderate staining, which was characterized by fine granules and focal linear surface and luminal staining (FIG. 6A). In fibrocystic disease, staining was much stronger in areas with epithelial hyperplasia than in areas without hyperplasia. When atypical hyperplasia was present, the intensity of staining within the epithelial cells increased as the degree of atypia increased (FIG. 6B). In malignant breast tissue there was marked increase in the intensity of staining and the number of cells stained (FIG. 6C). In most cases, the staining was characterized by coarse cytoplasmic granules. Circumferential staining of the cell surface was noted only in the malignant samples. Stroma in both benign and malignant samples showed weak diffuse staining which was accentuated around the lobular unit. The density of L-PHA reactive oligosaccharides appeared to increase in a progression from normal and benign breast tissue to epithelial hyperplasia.

The results of each case are summarized in Table III. Application of the student t test to the data in Table III indicated that L-PHA staining of the adenocarcinomas, and atypical ductal hyperplasia was significantly greater than in fibroadenoma specimens ($p=3\times10^6$ and $p<10^6$, respectively). However, staining of the non-atypical cases of ductal hyperplasia, which has a better prognosis than atypical cases, was not significantly different from the fibroadenomas.

EXAMPLE 13

Increased L-PHA reactivity by Lectin Histology Correlates with Disease Stage in Human Colorectal Carcinoma.

Figure 7A:
Figure 7B:
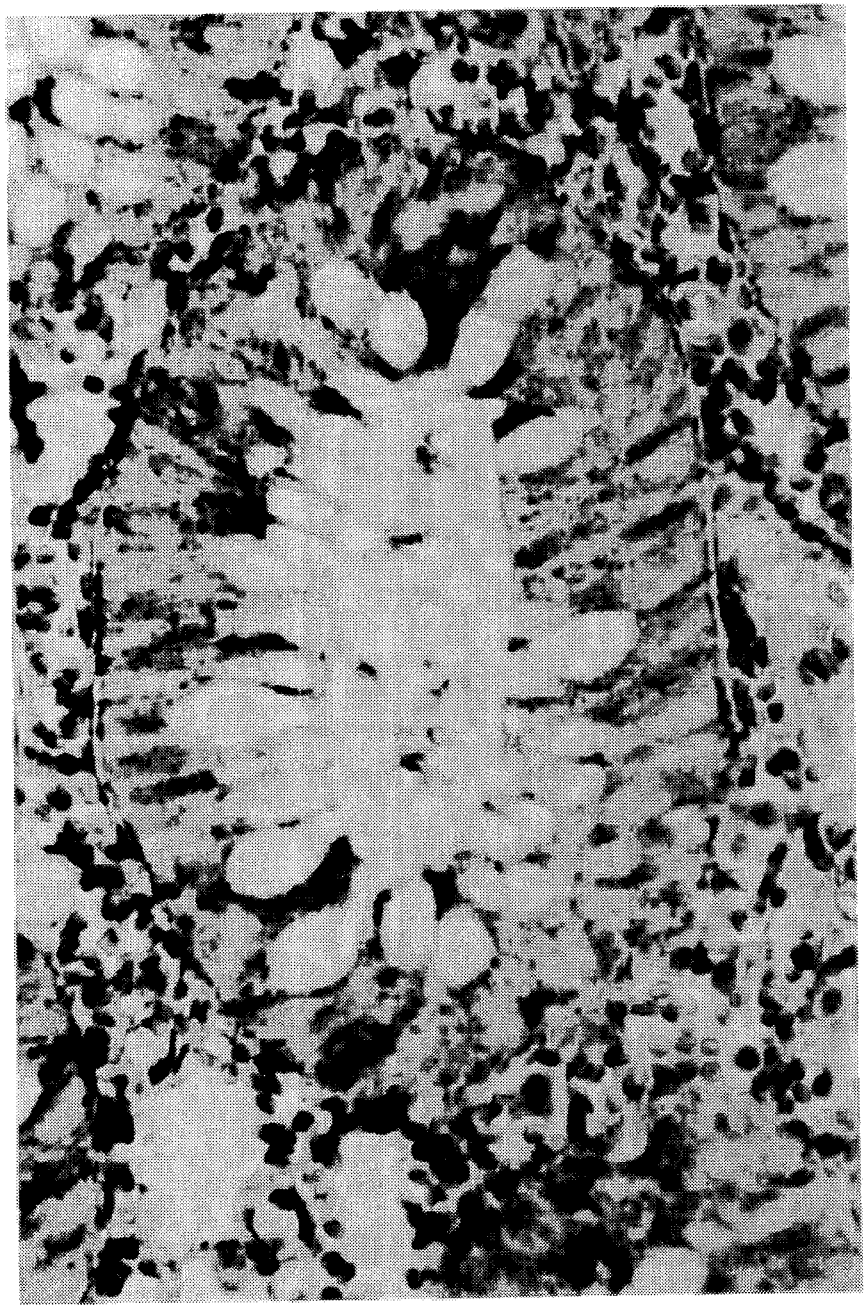
Figure 7C:

L-PHA reactive oligosaccharides were quantitated in histological sections of 18 colon carcinomas, 10 fibroadenomas and 20 normal tissue samples using the method set out in Example 11. FIG. 7 shows staining of normal colon (FIG. 7A); fibroadenoma (FIG. 7B) and colon carcinoma (FIG. 7C). Table IV shows the results of the detection of the colon malignancies by L-PHA lectin histology. The staging of polypous adenomas refers to tubular (T), villus (V) or a combination of tubular and villus (TV). The results shown in Table IV indicate that polypous adenomas have a small but significant increase in staining, while carcinomas are very much increased in L-PHA reactive oligosaccharides. The mean ±SD of the weighted scores for carcinoma, polypousadenoma, and normal tissues was 3.14 ±0.43, 2.07 ±0.25 and 1.56 ±0.21, respectively and these means are significantly different as determined by the student t test. ($P=2\times10^{-6}$).

The Wilcoxon rank sum test was used to compare the ABC Duke stages of colon carcinoma. The Duke's stage C tumors had significantly greater levels of staining than stage A tumors (p<0.05). The weighted scores for the two groups were 3.4 ±0.3 and 2.8 ±0.5. The median value for the +++category was 15% and 80%, respectively. The stage C Duke's classification denotes that metastases have been located in regional lymph nodes and the stage A tumors are confined to the primary site of growth. The observation that L-PHA staining is significantly higher in metastatic stage C tumors than in A stage carcinomas indicates that detection of these oligosaccharides in human tumors has prognostic value. Stage B tumors did not appear to be significantly different from either A or C; however, this may change when larger numbers of cases are examined.

EXAMPLE 14

L-PHA Reactivity in Malignant Melanoma.

Figure 8A:
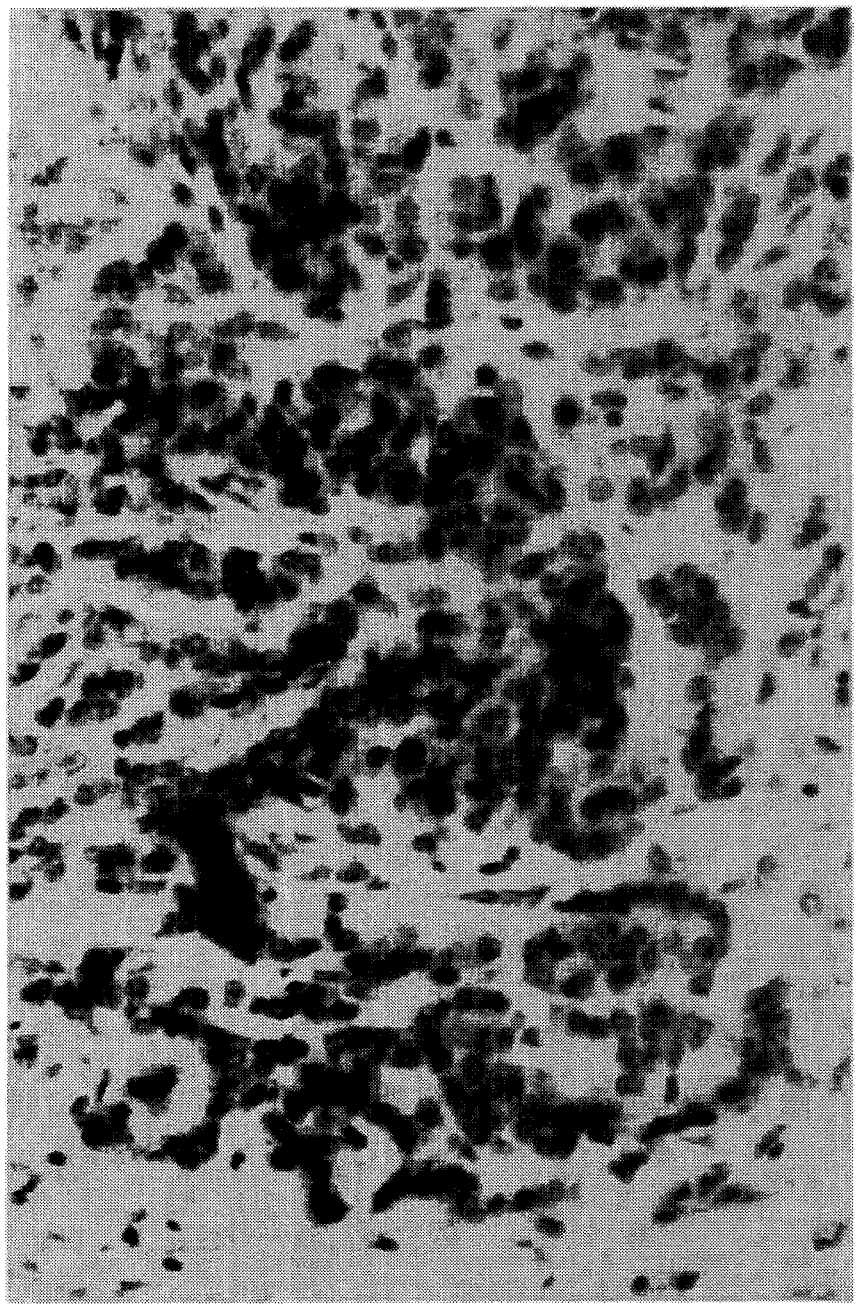
Figure 8B:
Figure 8C:

L-PHA staining intensity in histological sections of benign congenital nevus (FIG. 8A) was completely negative. In situ melanoma showed patches of stained tumor cells particularly at the basement membrane separating the dermis from the epidermis where the tumor has been confined (FIG. 8B). If this type of lesion is not surgically removed, it is quite likely to invade into the dermis becoming a malignant melanoma. L-PHA reactive tumor cells are present in this lesion and many appear to be located near the confining basement membrane where invasion by metastatic tumor cells occurs. Since the L-PHA reactive oligosaccharides appear to be required for metastasis in experimental animal models, L-PHA staining appears to detect nests of tumor cells with potential to metastasize prior to the event. Malignant melanoma showed increased staining with L-PHA compared to the in situ lesions (FIG. 8C). The cellular staining pattern in malignant melanomas was heterogeneous with regions of both intense and moderate staining.

TABLE III

Detection of Cancer and Atypical Hyperplasia in Breast by L-PHA Lectin Histology A. Breast Carcinomas

| Case No. | L-PHA Staining Intensity (% of cells) | | | | Weighted Score | Diagnosis | | | Invasive or in situ | Lymph node status |
|---|---|---|---|---|---|---|---|---|---|---|
| | +++ | ++ | + | 0 | | duct | lobular | muscinous | | |
| 1 | 100 | — | — | — | 4.0 | x | | | invasive | 0/15 |
| 2 | 100 | — | — | — | 4.0 | x | | | invasive | 0/12 |
| 3 | 5 | — | 95 | — | 2.1 | x | | | invasive | 3/3 |
| 4 | 95 | 5 | — | — | 3.95 | x | | | invasive | N.D. |
| 5 | 100 | — | — | — | 4.0 | x | | | invasive | 0/9 |
| 6 | 50 | — | 50 | — | 3.0 | x | | | invasive | 0/15 |
| 7 | 90 | 10 | — | — | 3.9 | x | | | invasive | 1/24 |
| 8 | 100 | — | — | — | 4.0 | x | | | invasive | N.D. |
| 9 | 90 | 10 | — | — | 3.9 | x | | | invasive | 2/23 |
| 10 | — | 75 | 25 | — | 2.85 | | | x | invasive | 0/18 |
| 11 | 100 | — | — | — | 4.0 | | | x | invasive | 4/4 |
| 12 | — | 75 | 25 | — | 2.85 | x | | | invasive | 1/13 |
| 13 | 90 | — | 10 | — | 3.8 | x | | | invasive | 0/22 |
| 14 | — | 50 | 50 | — | 2.5 | x | | | invasive | 0/19 |
| 15 | 90 | 10 | — | — | 3.9 | x | | | invasive | N.D. |
| 16 | 75 | 25 | — | — | 3.75 | x | | | in situ | N.D. |
| 17 | 100 | — | — | — | 4.0 | x | | | in situ | N.D. |
| 18 | 95 | 5 | — | — | 3.95 | x | | | in situ | N.D. |

N.D. not determined
Weighted score, mean ± SD. = 3.58 ± 0.62

B. Ductal Hyperplasia

| Case No. | L-PHA Staining Intensity (% of cells) | | | | Weighted Score | Degree of Ductal Hyperplasia | | |
|---|---|---|---|---|---|---|---|---|
| | +++ | ++ | + | 0 | | Non | Mild | Severe |
| 1 | — | — | 50 | 50 | 1.5 | x | | |
| 2 | — | 25 | 75 | — | 2.25 | x | | |
| 3 | — | — | 50 | 50 | 1.5 | x | | |
| 4 | — | 25 | 75 | — | 2.25 | x | | |
| 5 | — | — | 50 | 50 | 1.5 | | x | |
| 6 | — | 50 | 50 | — | 2.5 | | x | |
| 7 | 75 | 25 | — | — | 3.75 | | | x |
| 8 | 50 | — | 50 | — | 3.0 | | | x |
| 9 | — | 100 | — | — | 3.0 | | | x |
| 10 | — | 100 | — | — | 3.0 | | | x |
| 11 | 100 | — | — | — | 4.0 | | | x |
| 12 | 50 | 50 | — | — | 3.5 | | | x |
| 13 | — | 75 | 25 | — | 2.75 | | | x |
| 14 | — | 75 | 25 | — | 2.75 | | | x |
| 15 | 50 | 50 | — | — | 3.0 | | | x |
| 16 | 75 | 25 | — | — | 3.75 | | | x |

Weighted score, mean ± S.D. Cases 1–6 are 1.92 ± 0.47; cases 7–16 are 3.25 ± 0.21

C. Fibroadenoma

| Case No. | L-PHA Staining Intensity (% of cells) | | | | Weighted Score |
|---|---|---|---|---|---|
| | +++ | ++ | + | 0 | |
| 1 | — | — | 50 | 50 | 1.5 |
| 2 | — | 100 | — | — | 3.0 |
| 3 | — | — | 100 | — | 2.0 |

TABLE III-continued

Detection of Cancer and Atypical Hyperplasia in Breast by L-PHA Lectin Histology

| | | | | | |
|---|---|---|---|---|---|
| 4 | — | — | 25 | 75 | 1.25 |
| 5 | — | — | 50 | 50 | 1.5 |
| 6 | — | 50 | 50 | — | 2.5 |
| 7 | — | — | 100 | — | 2.0 |
| 8 | — | — | 75 | 25 | 1.75 |
| 9 | — | 75 | 25 | — | 2.75 |
| 10 | — | — | 50 | 50 | 2.5 |
| 11 | — | — | 50 | 50 | 1.5 |
| 12 | — | 25 | 75 | — | 2.25 |
| 13 | — | — | 50 | 50 | 2.5 |
| 14 | — | 25 | 75 | — | 2.25 |
| 15 | — | 50 | 50 | — | 2.5 |
| 16 | — | — | 25 | 75 | 1.25 |
| 17 | — | — | 25 | 75 | 1.25 |
| 18 | — | — | 25 | 75 | 1.25 |

Weighted score, meant ± S.D. = 1.97 ± 0.58

TABLE IV

Detection of Colon Malignancies by L-PHA Lectin Histology

A. Carcinomas

| Case No. | L-PHA Staining Intensity (% of cells) | | | | Weighted Score | Duke's Stage | Grade |
|---|---|---|---|---|---|---|---|
| | +++ | ++ | + | 0 | | | |
| 1 | 75 | 15 | — | 10 | 3.55 | B | 3 |
| 2 | — | 65 | 5 | 30 | 2.35 | A | 1 |
| 3 | 75 | 15 | — | 10 | 3.55 | C | 2 |
| 4 | — | 75 | 15 | 10 | 2.65 | B | 2 |
| 5 | 15 | 75 | — | 10 | 2.95 | A | 2 |
| 6 | 10 | 60 | 5 | 25 | 2.55 | B | 2 |
| 7 | 75 | 15 | — | 10 | 3.55 | B | 3 |
| 8 | 15 | 75 | — | 10 | 2.95 | A | 2 |
| 9 | 25 | 65 | — | 10 | 3.05 | C | 2 |
| 10 | 75 | 15 | — | 10 | 3.55 | A | 3 |
| 11 | 25 | 65 | — | 10 | 3.05 | C | 2 |
| 12 | 15 | 75 | — | 10 | 2.95 | A | 1 |
| 13 | 75 | 15 | — | 10 | 3.55 | C | 2 |
| 14 | 80 | 10 | — | 10 | 3.60 | C | 2 |
| 15 | 85 | 5 | — | 10 | 3.65 | C | 1 |
| 16 | 20 | 40 | 20 | 20 | 2.80 | B | 1 |
| 17 | 80 | 10 | — | 10 | 3.60 | C | 2 |
| 18 | 40 | 20 | 10 | 30 | 2.70 | C | 1 |

Weighted score, mean ± S.D. = 3.14 ± 0.43

C. Normal Colon

| Case No. | L-PHA Staining (% of cells) | | | | Weighted Score |
|---|---|---|---|---|---|
| | +++ | ++ | + | 0 | |
| 1 | — | 5 | 60 | 35 | 1.70 |
| 2 | — | 30 | 50 | 20 | 2.10 |
| 3 | — | 5 | 55 | 40 | 1.65 |
| 4 | — | 5 | 55 | 40 | 1.65 |
| 5 | — | 5 | 25 | 70 | 1.35 |
| 6 | — | 5 | 55 | 40 | 1.65 |
| 7 | — | 5 | 25 | 70 | 1.35 |
| 8 | — | 5 | 25 | 70 | 1.35 |
| 9 | — | 5 | 25 | 70 | 1.35 |
| 10 | — | 10 | 20 | 70 | 1.40 |
| 11 | — | — | 20 | 80 | 1.20 |
| 12 | — | 10 | 10 | 80 | 1.30 |
| 13 | — | 20 | 20 | 60 | 1.60 |
| 14 | — | 20 | 20 | 60 | 1.60 |
| 15 | 10 | 10 | 20 | 60 | 1.70 |
| 16 | — | 20 | 20 | 60 | 1.6 |
| 17 | — | 20 | 20 | 60 | 1.6 |
| 18 | 10 | 10 | 20 | 60 | 1.7 |
| 19 | — | 20 | 20 | 60 | 1.6 |
| 20 | 10 | 10 | 20 | 60 | 1.7 |

Weighted score, mean ± S.D. = 1.56 ± 0.21

B. Polyps adenomas

| Case No. | L-PHA Staining (% of cells) | | | | Weighted Score | Stage |
|---|---|---|---|---|---|---|
| | +++ | ++ | + | 0 | | |
| 1 | 5 | 5 | 50 | 40 | 1.75 | T |
| 2 | 15 | 15 | 50 | 20 | 2.25 | T |
| 3 | 5 | 5 | 55 | 35 | 1.80 | T |
| 4 | 15 | 25 | 40 | 20 | 2.35 | TV |
| 5 | 15 | 25 | 40 | 20 | 2.35 | V |
| 6 | 15 | 25 | 40 | 20 | 2.35 | TV |
| 7 | 5 | 15 | 60 | 20 | 2.05 | V |
| 8 | 5 | 10 | 60 | 25 | 1.95 | T |
| 9 | 5 | 15 | 60 | 20 | 2.05 | T |
| 10 | 0 | 5 | 65 | 30 | 1.75 | V |

Weighted score, mean ± S.D. = 2.07 ± 0.25

I claim:

1. A process for screening for a miligant tumor which comprises determining an amount of GlcNAc transferase V activity in a tumor sample which comprises reacting the GlcNAc transferase V in a tumor sample with an acceptor substrate and a sugar nucleotide donor to produce a detectable change, and detecting the change, wherein the acceptor substrate is an oligosaccharide, a glycopeptide or a glycoprotein having the structure GlcNAc β1-2Man α1-6Man β1-R$_1$, where R$_1$ is GlcNAc β1-4GlcNAc with or without fucose or a synthetic linker, and wherein the sugar nucleotide donor is uridine diphospho-N-acetylglycosamine, thereby determining the amount of GlCNAc transferase V activity in the sample, and determining if the tumor is malignant by comparing the amount of GlcNAc transferase V activity in the sample with an amount of GlcNAc transferase V activity associated with normal tissues or with known malignant tumors.

2. The process as claimed in claim 1, wherein the acceptor substrate is asialo-agalacto-fectuin glycopeptide.

3. The process as claimed in claim 1 wherein the tumor sample is tumor tissue removed from a patient, a tissue section of tumor tissue removed from a patient or a glycoprotein fraction separated from a tumor sample.

4. The process as claimed in claim 3 wherein the tumor sample is a cell lysate fraction prepared from the tumor tissue.

5. The process as claimed in claim 1 wherein the tumor sample from tumor removed from a patient with breast, colon, or skin cancer.

6. The process as claimed in claim 1 wherein the detectable change is detected with a labelled antibody specific for a reaction product of the GlcNAc transferase V, acceptor substrate and sugar nucleotide.

7. The process as claimed in claim 1 wherein the sugar nucleotide donor is labelled in the GlcNAc portion with radioactive or nonradioactive groups.

8. A diagnostic kit for screening for a malignant tumor comprising an acceptor substrate and a sugar nucleotide donor to interact with GlcNAc transferase V in a tumor sample to produce a detectable change, and means for detecting the change, wherein the acceptor substrate is an oligosaccharide, a glycopeptide or a glycoprotein having the structure GlcNA $\beta$1-2Man $\alpha$1-6Man $\beta$1-$R_1$, wherein $R_1$ is GlcNAc $\beta$1-4GlcNAc with or without fucose or a synthetic linker, wherein the sugar nucleotide donor is uridine disphospho-N-acetylglycosamine.

9. The diagnostic kit as claimed in claim 8 further comprising a buffer.

10. The diagnostic kit as claimed in claim 8 wherein the sugar nucleotide donor is labelled in the GlcNAc portion with radioactive or nonradioactive groups.

* * * * *